United States Patent
Liu et al.

(10) Patent No.: US 12,203,120 B2
(45) Date of Patent: Jan. 21, 2025

(54) METHOD FOR PRECISELY PREPARING CIRCULAR RNA WITH ANABAENA INTRON SELF-CLEAVING RIBOZYME

(71) Applicant: Guangzhou Geneseed Biotech Co., Ltd., Guangzhou (CN)

(72) Inventors: Ming Liu, Guangzhou (CN); Maolei Zhang, Guangzhou (CN); Yesheng Wang, Guangzhou (CN); Qiujie Cai, Guangzhou (CN); Wanjun Zhang, Guangzhou (CN); Xiaodan Ma, Guangzhou (CN)

(73) Assignee: Guangzhou Geneseed Biotech Co., Ltd., Guangzhou (CN)

( * ) Notice: Subject to any disclaimer, the term of this patent is extended or adjusted under 35 U.S.C. 154(b) by 0 days.

(21) Appl. No.: 18/430,378

(22) Filed: Feb. 1, 2024

(65) Prior Publication Data
US 2024/0247295 A1   Jul. 25, 2024

Related U.S. Application Data

(63) Continuation of application No. PCT/CN2023/085181, filed on Mar. 30, 2023.

(30) Foreign Application Priority Data

Jul. 6, 2022   (CN) .................. 202210787981.3

(51) Int. Cl.
*C12N 15/11*   (2006.01)
*C12N 15/64*   (2006.01)
*C12N 15/72*   (2006.01)
*C12P 19/34*   (2006.01)

(52) U.S. Cl.
CPC ............ *C12P 19/34* (2013.01); *C12N 15/111* (2013.01); *C12N 15/64* (2013.01); *C12N 15/72* (2013.01); *C12N 2310/124* (2013.01)

(58) Field of Classification Search
None
See application file for complete search history.

(56) References Cited

U.S. PATENT DOCUMENTS

2020/0080106 A1   3/2020   Anderson et al.

FOREIGN PATENT DOCUMENTS

| CN | 101679962 A | 3/2010 |
| CN | 111321143 A | 6/2020 |

OTHER PUBLICATIONS

Lorenz et al. Algortihms for Molecular Biology 6: 26, pp. 1-4 (Year: 2011).*
Universitat Wien, Theoretical Biochemistry Group, Institute for Theoretical Chemsitry, TBI-ViennaRNA package 2, retrieved online May 6, 2024, pp. 1-10, https://www.tbi.univie.ac.at/RNA/#intro (Year: 2024).*

* cited by examiner

*Primary Examiner* — Brian Whiteman
(74) *Attorney, Agent, or Firm* — George D. Morgan (57) ABSTRACT

The present invention relates to the technical field of nucleic acids, and in particular, to a method for precisely preparing a circular RNA with an *Anabaena* intron self-cleaving ribozyme. By redesigning a target nucleic acid sequence of a linear RNA, selecting a site suitable for precise cleavage by the intron self-cleaving ribozyme, and removing exon sequences from the *Anabaena* intron self-cleaving ribozyme, precise cyclization of RNAs after in vitro transcription is achieved. The method provided by the present invention solves the problem in the prior art that linear RNAs cannot be precisely cyclized during the process of generating circular RNAs in vitro, and provides an ideal in vitro preparation method for circular RNA applications.

6 Claims, 7 Drawing Sheets
Specification includes a Sequence Listing.

```
                               SEQUENCE LISTING

Sequence total quantity: 11
SEQ ID NO: 1            moltype = RNA   length = 313
FEATURE                 Location/Qualifiers
source                  1..313
                        mol_type = other RNA
                        note = Anabaena intronic self-cleaving ribozyme sequence
                        organism = synthetic construct
SEQUENCE: 1
tgcggaatgg tagacgctac ggacttaaat aattgagcct taaagaagaa attctttaag   60
tggatgctct caaactcagg gaaacctaaa tctagttata gacaaggcaa tcctgagcca  120
agccgaagta gtaattagta agttaacaat agatgactta caactaatcg aaggtgcag   180
agactcgacg ggagctaccc taacgtcaag acgagggtaa agagagagtc caattctcaa  240
agccaatagg cagtagcgaa agctgcaaga gaatgaaaat ccgttgacct taaacggtcg  300
tgtgggttca agt                                                     313

SEQ ID NO: 2            moltype = RNA   length = 246
FEATURE                 Location/Qualifiers
source                  1..246
                        mol_type = other RNA
                        note = artificial sequence
                        organism = synthetic construct
SEQUENCE: 2
attaatcatc atcctagccc taagtctggc ctatgagtga ctacaactca acggctacat   60
agaaaaatcc accccttacg agtgcggctt cgaccctata tccccgccc gcgtcccttt   120
ctccataaaa ttcttcttag tagctattac cttcttatta tttgatctag aaattgcct   180
cctttttaccc ctaccatgag ccctacaaac aactaacctg ccactaatag ttatgtcatc  240
cctctt                                                              246

SEQ ID NO: 3            moltype = RNA   length = 493
FEATURE                 Location/Qualifiers
source                  1..493
                        mol_type = other RNA
                        organism = synthetic construct
SEQUENCE: 3
aacaatagat gacttacaac taatcggaag gtgcagagac tcgacgggag ctaccctaac   60
gtcaagacga gggtaaagag agagtccaat tctcaaagcc aataggcagt agcgaaagct  120
gcaagagaat gattaatcat catcctagcc taagtctgg cctatgagtg actacaactc   180
aacggctaca tagaaaaatc caccccttac gagtgcggct tcgaccctat atccccgcc   240
cgcgtccctt tctccataaa attcttctta gtagctatta ccttcttatt atttgatcta   300
gaaattgccc tccttttacc cctaccatga gccctacaaa caactaacct gccactaata   360
gttatgtcat ccctcttaaa taattgagcc ttaaagaaga aattctttaa gtggatgctc   420
tcaaactcag ggaaacctaa atctagttat agacaaggca atcctgagcc aagccgaagt   480
agtaattagt aag                                                      493

SEQ ID NO: 4            moltype = DNA   length = 18
FEATURE                 Location/Qualifiers
source                  1..18
                        mol_type = other DNA
                        organism = synthetic construct
SEQUENCE: 4
cacggacaga ccgccggc                                                  18

SEQ ID NO: 5            moltype = DNA   length = 18
FEATURE                 Location/Qualifiers
source                  1..18
                        mol_type = other DNA
                        organism = synthetic construct
SEQUENCE: 5
gccggcggtc tgtccgtg                                                  18

SEQ ID NO: 6            moltype = DNA   length = 20
FEATURE                 Location/Qualifiers
source                  1..20
                        mol_type = other DNA
                        organism = synthetic construct
SEQUENCE: 6
taatacgact cactataggg                                                20

SEQ ID NO: 7            moltype = DNA   length = 561
FEATURE                 Location/Qualifiers
source                  1..561
                        mol_type = other DNA
                        organism = synthetic construct
```

```
SEQUENCE: 7
ggatcctaat acgactcact atagggcacg gacagaccgc cggcaacaat agatgactta    60
caactaatcg gaaggtgcag agactcgacg ggagctaccc taacgtcaag acgagggtaa  120
agagagagtc caattctcaa agccaatagg cagtagcgaa agctgcaaga gaatgattaa  180
tcatcatcct agccctaagt ctggcctatg agtgactaca actcaacggc tacatagaaa  240
aatccacccc ttacgagtgc ggcttcgacc ctatatcccc cgcccgcgtc cctttctcca  300
taaaattctt cttagtagct attaccttct tattatttga tctagaaatt gccctccttt  360
taccccctacc atgagcccta caaacaacta acctgccact aatagttatg tcatccctct  420
taaataattg agccttaaag aagaaattct ttaagtggat gctctcaaac tcagggaaac  480
ctaaatctag ttatagacaa ggcaatcctg agccaagccg aagtagtaat tagtaaggcc  540
ggcggtctgt ccgtggaatt c                                            561

SEQ ID NO: 8        moltype = DNA   length = 20
FEATURE             Location/Qualifiers
source              1..20
                    mol_type = other DNA
                    organism = synthetic construct
SEQUENCE: 8
ctccttttac ccctaccatg                                              20

SEQ ID NO: 9        moltype = DNA   length = 18
FEATURE             Location/Qualifiers
source              1..18
                    mol_type = other DNA
                    organism = synthetic construct
SEQUENCE: 9
gatatagggt cgaagccg                                                18

SEQ ID NO: 10       moltype = RNA   length = 15
FEATURE             Location/Qualifiers
source              1..15
                    mol_type = other RNA
                    organism = synthetic construct
SEQUENCE: 10
agacgctacg gactt                                                   15

SEQ ID NO: 11       moltype = RNA   length = 45
FEATURE             Location/Qualifiers
source              1..45
                    mol_type = other RNA
                    organism = Synthetic construct
SEQUENCE: 11
taatagttat gtcatccctc ttattaatca tcatcctagc cctaa                  45
```

METHOD FOR PRECISELY PREPARING CIRCULAR RNA WITH ANABAENA INTRON SELF-CLEAVING RIBOZYME

CROSS-REFERENCE TO RELATED APPLICATIONS

The application claims priority to Chinese patent application No. 2022107879813, filed on Jul. 6, 2022, the entire contents of which are incorporated herein by reference.

SEQUENCE LISTING

The sequence listing xml file submitted herewith, named "WI_US24_13234_P.xml", created on Apr. 10, 2024, and having a file size of 12,788 bytes, is incorporated by reference herein.

TECHNICAL FIELD

The present invention relates to the technical field of nucleic acids, and in particular, to a method for precisely preparing a circular RNA with an *Anabaena* intron self-cleaving ribozyme.

BACKGROUND

With the progress of high-throughput sequencing technologies and bioinformatic analysis methods, researchers have discovered a large number of objectively existing circular RNA molecules in many organisms. Circular RNAs are closely related to the occurrence and development of many diseases. Previous research has reported that a circular RNA is a non-coding RNA molecule and acts as a sponge by interacting with a miRNA to play a role in regulating gene expression. With the deepening of research, it is found that circular RNAs can play a role in many ways. Circular RNAs can not only regulate gene transcription by interacting with genomic DNAs but also inhibit protein activity, collect components of a protein complex, or regulate protein activity by combining proteins. In addition, circular RNAs can serve as a translation template to be directly translated into functional polypeptides or proteins.

In recent years, mRNAs, as a protein replacement therapy, are widely used. By artificially designing and adding 5'UTR, 3'UTR, and polyadenylate sequences to the upstream and downstream of a protein-coding nucleic, a therapeutic mRNA can be assembled in vitro and then efficiently generate a target protein in vivo, thereby realizing a gene therapy for treating some genetic diseases; and the nucleic acid-modified artificial mRNA can efficiently generate an antigenic protein in vivo so that it can be applied to the development of vaccines for various infectious diseases. A linear mRNA has exposed 5'- and 3'-end sequences, making it very unstable both in vitro and in vivo, and have a short half-life, thereby greatly limiting its application. A circular RNA does not have 5' or 3' ends, making it tolerable of RNA enzyme degradation and more stable than linear mRNA molecules. Artificially designed circular RNAs can efficiently translate target polypeptides or proteins in cells without the need for special nucleic acid modifications. Furthermore, compared to linear mRNA molecules, circular RNAs have fewer side effects on host immunity.

Currently, common methods for preparing a circular RNA by in vitro transcription are mainly to generate linear RNAs in vitro and then connect and cyclize them through enzymatic ligation and cleavage of self-cleaving ribozymes. RNAs can be cyclized effectively by cyclizing linear RNAs through enzymatic ligation with a T4 DNA ligase, a T4 RNA ligase 1, a T4 RNA ligase 2, and the like. However, such methods require the use of additional splints or artificial selection of internal secondary structures as an aid to achieve effective cyclization and also have high technical requirements for users. For circular RNAs prepared by the conventional method of intron self-cleavage, it is necessary to add an exon sequence to both sides of a target molecule to cyclize it and the added exon sequence will be introduced into the target circular RNA sequence, ultimately resulting in large fragments of useless sequences in the target circular RNA. Some researchers have reported that circular RNAs can be precisely prepared by artificially designing and selecting the start and end base sequences of the target molecule and using the T4 phage intron self-cleaving system (Nucleic Acids Research, 2021, Vol. 49, No. 6e35), but this method has low preparation efficiency and is difficult to meet the requirements for large-scale industrial preparation. Therefore, it is necessary to establish a method that is easy to operate and capable of precisely preparing a circular RNA.

The Chinese patent CN111321143A discloses a method for preparing a circular RNA, which can reduce difficulty in the subsequent purification process and significantly suppress the production of macromolecular by-products during the cyclization process. However, this method may make errors when simulating the secondary structure of a linear RNA, designing a disconnection site, and performing the subsequent connection process, thereby reducing the accuracy of the formed circular RNA.

The Chinese patent CN101679962A discloses a single-stranded circular RNA and a preparation method therefor. This preparation method is only suitable for preparing a very short and small interfering siRNA but not suitable for preparing a circular RNA with large fragments and must contain both sense strand sequences and antisense strand sequences (which can be paired to form branches) as well as cyclization sequences. Therefore, this method has a low scope of application and cannot achieve the large-scale preparation of circular RNAs with large fragments.

To sum up, existing methods for preparing a circular RNA generally have problems such as low efficiency, complex preparation processes, and insufficient accuracy.

SUMMARY

In view of the forgoing common defects in the prior art, the present invention provides a method for precisely preparing a circular RNA with an *Anabaena* intron self-cleaving ribozyme. By designing and selecting target molecules and removing exon sequences from the *Anabaena* intron self-cleaving ribozyme, precise cyclization of RNAs after in vitro transcription is achieved, providing an ideal in vitro preparation method for circular RNA applications.

A technical solution adopted by the present invention is as follows:
  a method for precisely preparing a circular RNA with an *Anabaena* intron self-cleaving ribozyme, including:
  S1: analyzing a secondary structure of the *Anabaena* intron self-cleaving ribozyme using nucleic acid secondary structure analysis software RNAfold, and screening out sequences in upstream and downstream exons that are closely related to the activity of the self-cleaving ribozyme;
  S2: selecting an artificial sequence containing the sequences screened out in the step S1, inverting original upstream and downstream intron sequences of the *Anabaena*, and then replacing an original exon sequence in the *Anabaena* intron self-cleaving ribozyme with the artificial sequence to form an *Anabaena* intron self-cleaving frame for precisely preparing the circular RNA;

S3: adding an 18-base reverse complementary sequence to each of the upstream and downstream of the *Anabaena* intron self-cleaving frame sequence obtained in the step S2, and then adding a T7 transcription promoter to both sides of the sequence and a restriction endonuclease cleavage site to both ends of the sequence to form a total linear RNA sequence, and finally introducing the total linear RNA sequence into a pUC19 skeleton vector to prepare a plasmid;

S4: digesting the plasmid obtained in the step S3 with an endonuclease EcoRI to obtain a linearized plasmid, performing purification, obtaining a transcribed linear RNA through in vitro transcription and DNA template digestion, and performing purification again to obtain a purified transcribed linear RNA; and S5: cyclizing the purified transcribed linear RNA obtained in the step S4 in vitro and performing purification to obtain a purified cyclized RNA, and further performing tolerance testing and circular RNA cyclization interface verification to obtain the circular RNA.

Preferably, the *Anabaena* intron self-cleaving ribozyme described in the step S1 has a sequence with the GenBank accession number of AY768517 and shown as SEQ ID NO. 1; and the sequences in upstream and downstream exons that are closely related to the activity of the self-cleaving ribozyme are an end sequence CUU and a start base A, respectively.

```
                                       (SEQ ID NO. 1)
5'UGCGGAAUGGUAGACGCUACGGACUUAAAUAAUUGAGCCUUAAAGA

AGAAAUUCUUUAAGUGGAUGCUCUCAAACUCAGGGAAACCUAAAUCUAGU

UAUAGACAAGGCAAUCCUGAGCCAAGCCGAAGUAGUAAUUAGUAAGUUAA

CAAUAGAUGACUUACAACUAAUCGGAAGGUGCAGAGACUCGACGGGAGCU

ACCCUAACGUCAAGACGAGGGUAAAGAGAGAGUCCAAUUCUCAAAGCCAA

UAGGCAGUAGCGAAAGCUGCAAGAGAAUGAAAAUCCGUUGACCUUAAACG

GUCGUGUGGGUUCAAGU3';
```

Preferably, the artificial sequence described in the step S2 is shown as SEQ ID NO. 2; and the sequence of the prepared *Anabaena* intron self-cleaving frame is shown as SEQ ID NO. 3.

```
                                       (SEQ ID NO. 2)
AUUAAUCAUCAUCCUAGCCCUAAGUCUGGCCUAUGAGUGACUACAACU

CAACGGCUACAUAGAAAAAUCCACCCCUUACGAGUGCGGCUUCGACCCUA

UAUCCCCCGCCCGCGUCCCUUUCUCCAUAAAAUUCUUCUUAGUAGCUAUU

ACCUUCUUAUUAUUUGAUCUAGAAAUUGCCCUCCUUUUACCCCUACCAUG

AGCCCUACAAACAACUAACCUGCCACUAAUAGUUAUGUCAUCCCUCUU;

(SEQ ID NO. 3)
5'AACAAUAGAUGACUUACAACUAAUCGGAAGGUGCAGAGACUCGACG

GGAGCUACCCUAACGUCAAGACGAGGGUAAAGAGAGAGUCCAAUUCUCAA
```

```
-continued
AGCCAAUAGGCAGUAGCGAAAGCUGCAAGAGAAUGAUUAAUCAUCAUCCU

AGCCCUAAGUCUGGCCUAUGAGUGACUACAACUCAACGGCUACAUAGAAA

AAUCCACCCCUUACGAGUGCGGCUUCGACCCUAUAUCCCCCGCCCGCGUC

CCUUUCUCCAUAAAAUUCUUCUUAGUAGCUAUUACCUUCUUAUUAUUUGA

UCUAGAAAUUGCCCUCCUUUUACCCCUACCAUGAGCCCUACAAACAACUA

ACCUGCCACUAAUAGUUAUGUCAUCCCUCUUAAAUAAUUGAGCCUUAAAG

AAGAAAUUCUUUAAGUGGAUGCUCUCAAACUCAGGGAAACCUAAAUCUAG

UUAUAGACAAGGCAAUCCUGAGCCAAGCCGAAGUAGUAAUUAGUAAG

3';
```

Preferably, the upstream 18-base sequence described in the step S3 is shown as SEQ ID NO. 4, and the downstream 18-base sequence is shown as SEQ ID NO. 5; the sequence of the T7 transcription promoter is shown as SEQ ID NO. 6; and the total linear RNA sequence is shown as SEQ ID NO. 7.

```
                                       (SEQ ID NO. 4)
CACGGACAGACCGCCGGC;

(SEQ ID NO. 5)
GCCGGCGGTCTGTCCGTG;

(SEQ ID NO. 6)
TAATACGACTCACTATAGGG;

(SEQ ID NO. 7)
5'GGATCCTAATACGACTCACTATAGGGCACGGACAGACCGCCGGCAACA

ATAGATGACTTACAACTAATCGGAAGGTGCAGAGACTCGACGGGAGCTAC

CCTAACGTCAAGACGAGGGTAAAGAGAGAGTCCAATTCTCAAAGCCAATA

GGCAGTAGCGAAAGCTGCAAGAGAATGATTAATCATCATCCTAGCCCTAA

GTCTGGCCTATGAGTGACTACAACTCAACGGCTACATAGAAAAATCCACC

CCTTACGAGTGCGGCTTCGACCCTATATCCCCCGCCCGCGTCCCTTTCTC

CATAAAATTCTTCTTAGTAGCTATTACCTTCTTATTATTTGATCTAGAAA

TTGCCCTCCTTTTACCCCTACCATGAGCCCTACAAACAACTAACCTGCCA

CTAATAGTTATGTCATCCCTCTTAAATAATTGAGCCTTAAAGAAGAAATT

CTTTAAGTGGATGCTCTCAAACTCAGGGAAACCTAAATCTAGTTATAGAC

AAGGCAATCCTGAGCCAAGCCGAAGTAGTAATTAGTAAGGCCGGCGGTCT

GTCCGTGGAATTC 3'.
```

Preferably, the upstream and downstream restriction endonuclease cleavage sites described in the step S3 are a BamHI restriction endonuclease cleavage site and an EcoRI restriction endonuclease cleavage site, respectively.

Preferably, the linearized plasmid described in the step S4 is obtained as follows: construct a digestion system of 200 μL containing 20 μg of plasmids, 20 μL of 10×Buffer, 10 μL of the endonuclease EcoRI, and DEPC-H2O complementing to 200 μL, and then allow the digestion system to react at 37° C. for 2 h, and finally store the obtained linearized plasmid at 4° C.

Preferably, the in vitro cyclization of the linear RNA described in the step S5 is achieved as follows: construct a cyclization system of 400 μL containing GTPs with a final concentration of 0.2 mM, linear RNAs with a final concentration of 2~8 μg/μL, 40 μL of 10×buffer, and DEPC-H2O;

mix the cyclization system uniformly and allow it to react at 42° C. or 55° C. for 6 h; finally store the obtained circular RNA at 4° C.

The present invention further provides a precise circular RNA obtained by the above-described method.

The conventional method of using the *Anabaena* intron self-cleaving ribozyme requires the aid of two internal exon sequences for self-cleavage to generate the target circular RNA, and these two large-fragment exon sequences are introduced into the sequence of the target RNA. By analyzing the sequence of the *Anabaena* intron self-cleaving ribozyme, the present invention found that the target circular RNA could be generated through precise cleavage only by reasonably selecting the start and end base sequences of the target molecule.

Compared to the prior art, the method for precisely preparing a circular RNA with an *Anabaena* intron self-cleaving ribozyme provided by the present invention has the following advantages: the method provided by the present invention is easy to operate, capable of achieving the precise cyclization of RNAs after in vitro transcription, and suitable for the large-scale preparation of circular RNAs, providing an ideal in vitro preparation method for circular RNA applications.

DETAILED DESCRIPTION OF THE EMBODIMENTS

The present invention is further explained below with reference to embodiments, but it should be noted that the following embodiments are only used to explain the present invention rather than to limit the present invention, and all technical solutions identical or similar to the present invention fall within the protection scope of the present invention. Where no specific techniques or conditions are noted in the embodiments, operations are performed according to conventional technical methods and content of instrument specifications in the art; and where no manufacturers are noted for reagents or instruments used herein, they are all conventional commercially available products.

Figure 1:
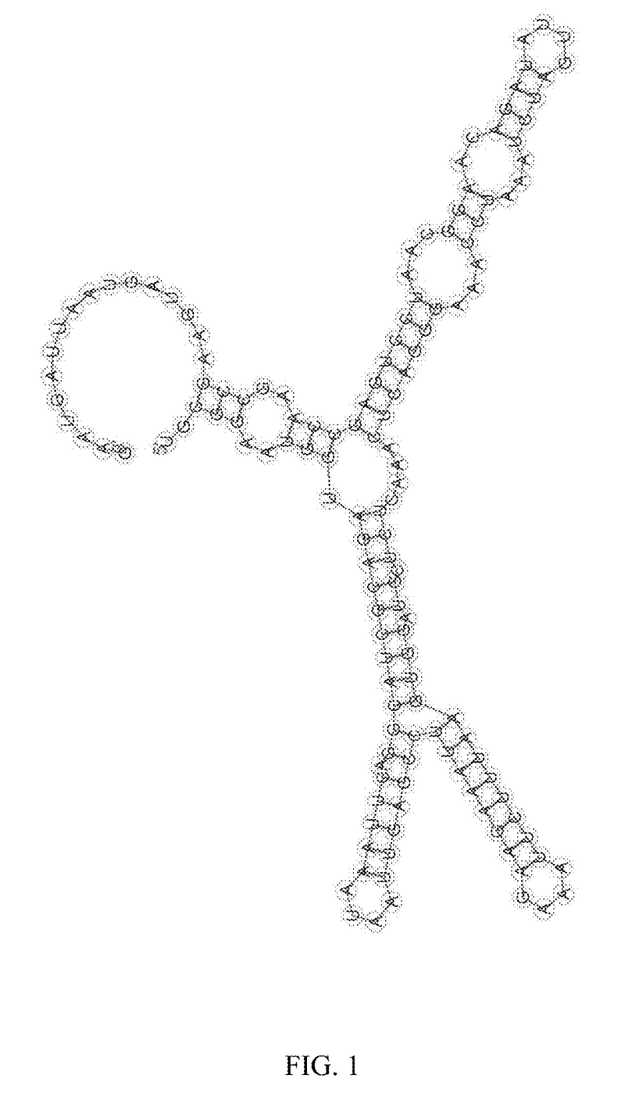
FIG. 1 is a diagram of secondary structures of an upstream intron and an upstream exon of an *Anabaena* intron self-cleaving ribozyme (SEQ ID NO. 1, bases 1-26 constitute the upstream exon sequence, bases 27-142 constitute the upstream intron sequence)
Figure 2:
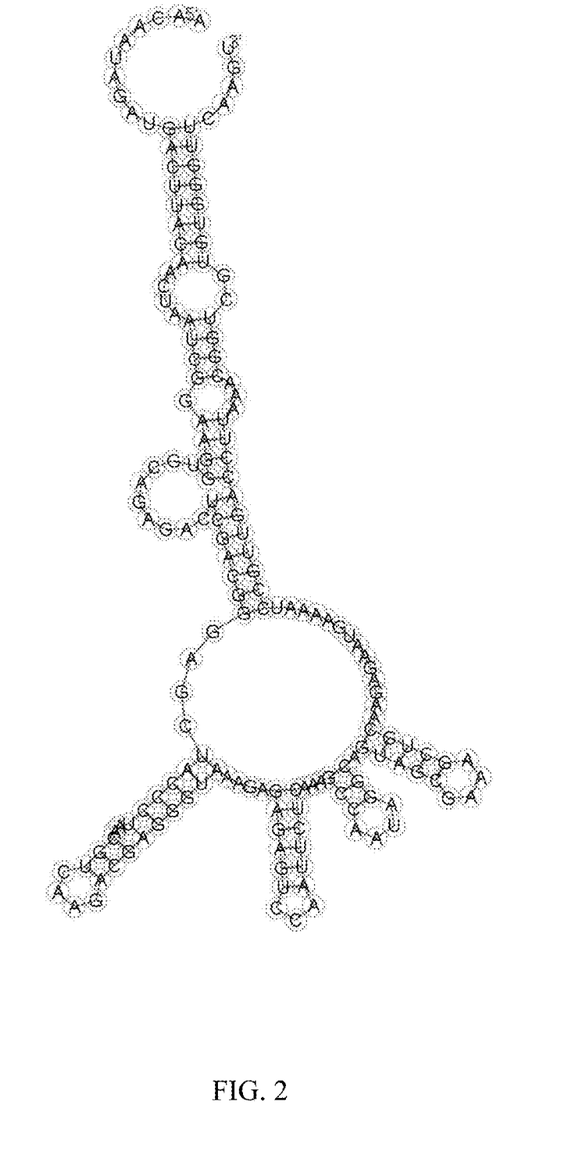
FIG. 2 is a diagram of secondary structures of a downstream exon and a downstream intron of an *Anabaena* intron self-cleaving ribozyme (SEQ ID NO. 1, bases 145-275 constitute the downstream intron sequence, bases 276-313 constitute the downstream exon sequence)

Embodiment: A Method for Precisely Preparing a Circular RNA with an *Anabaena* Intron Self-Cleaving Ribozyme S1: a secondary structure of the *Anabaena* intron self-cleaving ribozyme was analyzed using nucleic acid secondary structure analysis software RNAfold, and sequences in upstream and downstream exons that are closely related to the activity of the self-cleaving ribozyme were screened out;

The *Anabaena* intron self-cleaving ribozyme has a sequence with the GenBank accession number of AY768517 and shown as SEQ ID NO. 1; the total length of the sequence is 313 bases; the bases 1-26 constitute an upstream exon sequence, the bases 27-142 constitute an upstream intron sequence, the bases 143-144 constitute an spacer sequence, the bases 145-275 constitute a downstream intron sequence, and the bases 276-313 constitute a downstream exon sequence; the structure of the *Anabaena* intron self-cleaving ribozyme was analyzed as follows with nucleic acid secondary structure analysis software RNAfold (FIGS. 1 and 2); it was found from the secondary structure analysis of the of the sequence that there was a fragment of AGACGC-UACGGACUU (SEQ ID NO.10) (bases 11-26) in the upstream exon sequence, especially an end CUU sequence (bases 24-26) and the bases in the intron formed a pairing structure, indicating that the end sequence CUU in the upstream exon may be closely related to the activity of the *Anabaena* intron self-cleaving ribozyme; and the structural analysis of the downstream intron and the downstream exon as shown in FIG. 2 shows that no paired domains closely related to cleavage activity were found, and the structure indicates that the start base A of the downstream exon may be closely related to the activity of the self-cleaving ribozyme.

S2: an artificial sequence containing the sequences screened out in the step S1 was selected, original upstream and downstream intron sequences of the *Anabaena* were inverted, and then an original exon sequence in the *Anabaena* intron self-cleaving ribozyme was replaced with the artificial sequence to form an *Anabaena* intron self-cleaving frame for precisely preparing the circular RNA:

An artificial sequence-246 nt (SEQ ID NO.2) was selected as a case to test the cyclization effect of the *Anabaena* intron self-cleaving ribozyme on the target molecule. Based on the analysis of the secondary structure of the *Anabaena* intron self-cleaving ribozyme, the principle proposed by the present invention is that the first start base of the target molecule used for cyclization is A and the last three bases are CUU as a preferred base sequence.

The original upstream and downstream intron sequences of the *Anabaena* were inverted, and then an original exon sequence in the *Anabaena* intron self-cleaving ribozyme was replaced with the artificial sequence-246 nt to form an *Anabaena* intron self-cleaving frame (SEQ ID NO. 3) for precisely preparing the circular RNA, which is designated sequence-3 as follows: in the sequence-3, the bases 1-131 constitute the downstream intron of the original sequence of the *Anabaena*, the bases 132-377 constitute the artificially inserted test sequence (artificial sequence-246 nt), and the bases 388-493 constitute the upstream intron sequence of the original sequence of the *Anabaena*.

S3: adding an 18-base reverse complementary sequence to each of the upstream and downstream of the *Anabaena* intron self-cleaving frame sequence obtained in the step S2, and then adding a T7 transcription promoter to both sides of the sequence and a restriction endonuclease cleavage site to both ends of the sequence to form a total linear RNA sequence, and finally introducing the total linear RNA sequence into a pUC19 skeleton vector to prepare a plasmid;

Based on the sequence-3, to make the upstream and downstream introns of the *Anabaena* closer to each other, an 18-base reverse complementary sequence (SEQ ID NO. 4-5) was added to each of the upstream and downstream, and then a T7 transcription promoter (SEQ ID NO. 6) was added to both sides of the sequence and a restriction endonuclease cleavage site (BamHI and EcoRI) were added to both ends of the sequence to form a plasmid template sequence transcribed by the artificial sequence-246 nt in vitro, which was designated sequence-4 (SEQ ID NO. 7) and obtained by the method of whole gene chemosynthesis entrusted to be carried out by GUANGZHOU IGE BIOTECHNOLOGY LTD., and then the fragment was introduced into a pUC19 skeleton vector through the two endonuclease cleavage sites BamHI and EcoRI.

In the sequence-4, the bases 1-6 constitute the BamHI endonuclease cleavage site, the bases 7-26 constitute the T7 promoter sequence, the bases 27-44 constitute a paired sequence of the upstream 18 bases, the bases 45-175 constitute the downstream intron sequence of the *Anabaena*, the bases 176-421 constitutes the fragment of the artificially inserted sequence-246 nt, the bases 422-537 constitutes the downstream intron sequence of the *Anabaena*, the bases 538-555 constitutes a paired sequence of the downstream 18 bases, and the bases 556-561 constitutes the EcoRI endonuclease cleavage site sequence.

S4: the plasmid obtained in the step S3 was digested with an endonuclease EcoRI to obtain a linearized plasmid, purification was performed, a transcribed linear RNA was obtained through in vitro transcription and DNA template digestion, and purification was performed again to obtain a purified transcribed linear RNA;

As shown in Table 1 below, the plasmid was digested with the endonuclease EcoRI to obtain the linearized plasmid:

TABLE 1

Linearized Plasmid Preparation System

| Component | Usage amount |
| --- | --- |
| Plasmid | 20 μg |
| 10× Buffer | 20 μL |
| Endonuclease EcoRI | 10 μL |
| DEPC-H$_2$O | Up to 200 μL |

The components were slightly blown, sucked, and mixed with a pipette to allow a reaction at 37° C. for 2 h and hold at 4° C.

The product obtained after the digestion was purified by a phenol/chloroform method as follows:
(1) 200 μL of phenol/chloroform mixed solution (1:1) at pH 7-8 was added into 200 μL of the sample for extraction, a mixture thereof was centrifuged at 13,000 g for 5 min, and the upper-layer solution (aqueous phase) was transferred to a new RNase-free EP tube;
(2) chloroform with the same volume as the aqueous phase was added into the new RNase-free EP tube, extraction was performed twice, and the upper-layer aqueous phase was collected;
(3) anhydrous ethanol with a volume two times that of the upper-layer aqueous phase was added into the collected upper-layer aqueous phase for uniform mixing, incubation was performed at −20° C. for more than 30 min, centrifugation was performed at 13,000 g, 4° C. for 10 min, the supernatant was discarded, and the precipitate was retained;
(4) 500 μL of 70% ethanol prepared with pre-cooled DEPC-H2O was added to the precipitate for uniform vortex mixing, centrifugation was performed at 13,000 g, 4° C. for 10 min, and the supernatant was discarded;
(5) the cover was opened for drying for 2 min, and 30 μL of DEPC-H2O was added for dissolution; and
(6) the concentration and mass of the linearized plasmid were measured using NanoDrop, and the product was stored at −80° C.

In vitro transcription process: the reaction system for in vitro transcription was prepared according to Table 2

TABLE 2

Reaction System of In Vitro Transcription

| Component | Usage amount |
| --- | --- |
| 10× Reaction buffer | 2 μL |
| 25 mM NTP | 8 μL |
| 500 mM GMP | 2 μL |
| RNA inhibitor (40 U/μL) | 1 μL |
| Pyrophosphatase, Inorganic(0.1 U/μL) | 0.4 μL |
| T7 RNA polymerase | 2 μL |
| DNA template | 1 μL |
| DEPC-H$_2$O | Up to 20 μL |

The components were slightly blown, sucked, and mixed with a pipette to allow a reaction at 37° C. for 2 h and hold at 4° C.

DNA Template Digestion

After the transcription was completed, 2 μL of RNase-free DNase was added to 20 μL of the product and a mixture thereof was gently and uniformly mixed with a pipette to allow a reaction at 37° C. for 15 min.

Then the transcribed linear RNA was purified again by the lithium chloride precipitation method as follows:
(1) 30 μL of RNase-free H2O and 25 μL of LiCl (8M, RNase-free) were added to 20 μL of the reaction mixture;
(2) after uniform mixing, the mixture was placed at −20° C. for at least 30 min, centrifugation was performed at 13,000 g, 4° C. for 15 min, and the precipitate was collected;
(3) 500 μL of 70% ethanol pre-cooled with ice was added to wash the RNA precipitate; and
(4) the RNA precipitate was dissolved with 20 μL of RNase-free H2O, and the purified RNA solution was stored at −80° C.

S5: the purified transcribed linear RNA obtained in the step S4 was cyclized in vitro and purification was performed to obtain a purified cyclized RNA, and then tolerance testing and circular RNA cyclization interface verification were further performed to obtain the circular RNA. The RNA cyclization reaction system was prepared according to Table 3.

TABLE 3

| Component | Usage amount |
| --- | --- |
| \multicolumn{2}{c}{Preparation of Linear RNA (that is, linear precursor RNA) Cyclization System} | |
| GTP | Final concentration 0.2 mM |
| Final concentration of linear precursor RNA | 1, 2, 4, 8 μg/μL |
| 10× Buffer | 40 μL |
| DEPC-H$_2$O | Total system 400 μL |

The above reaction solution was mixed uniformly to allow a reaction at 70° C. for 3 min first and then at 37° C., 42° C., and 55° C. respectively for 6 h, and finally stored at 4° C.

Figure 3:
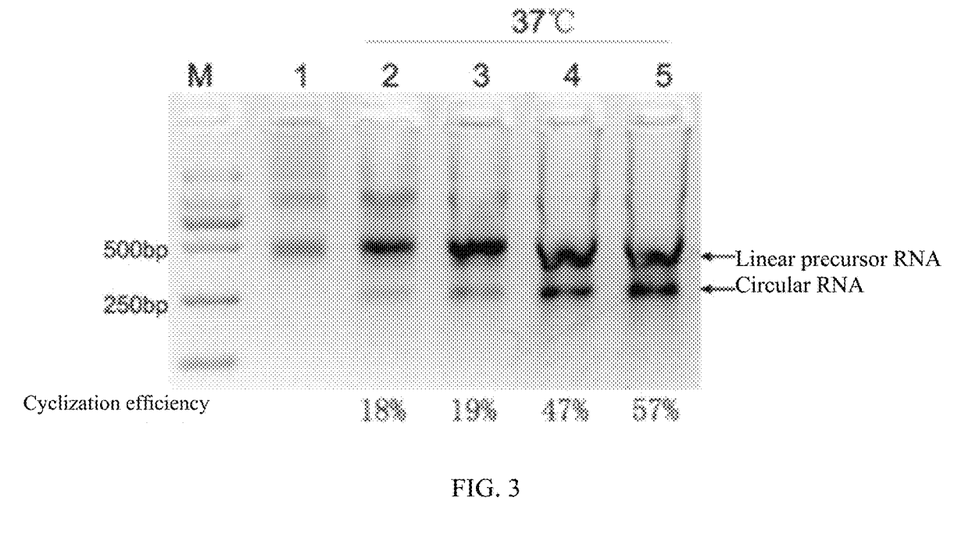
FIG. 3 is a diagram of nucleic acid electrophoresis detection of a circular RNA prepared with an *Anabaena* intron self-cleaving ribozyme at 37° C.
Figure 4:
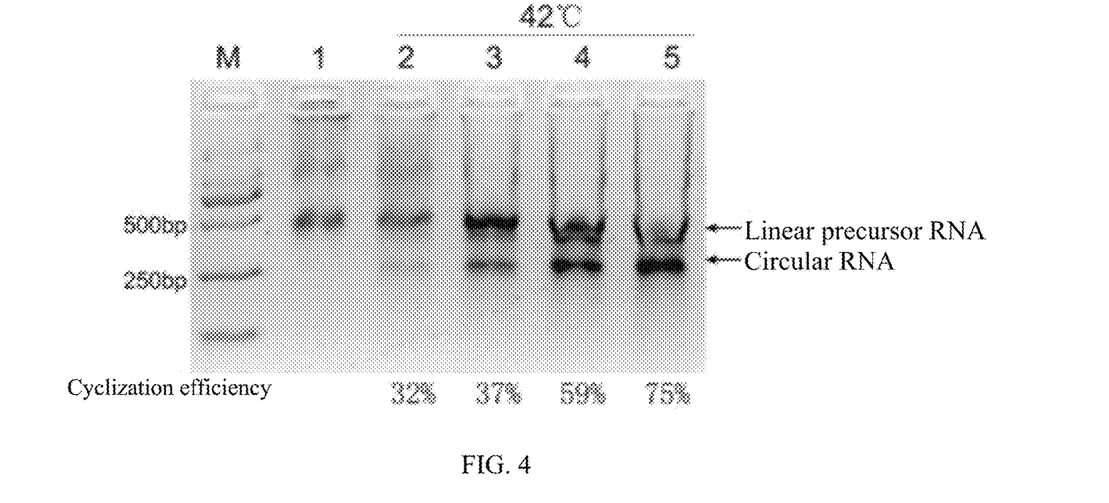
FIG. 4 is a diagram of nucleic acid electrophoresis detection of a circular RNA prepared with an *Anabaena* intron self-cleaving ribozyme at 42° C.
Figure 5:
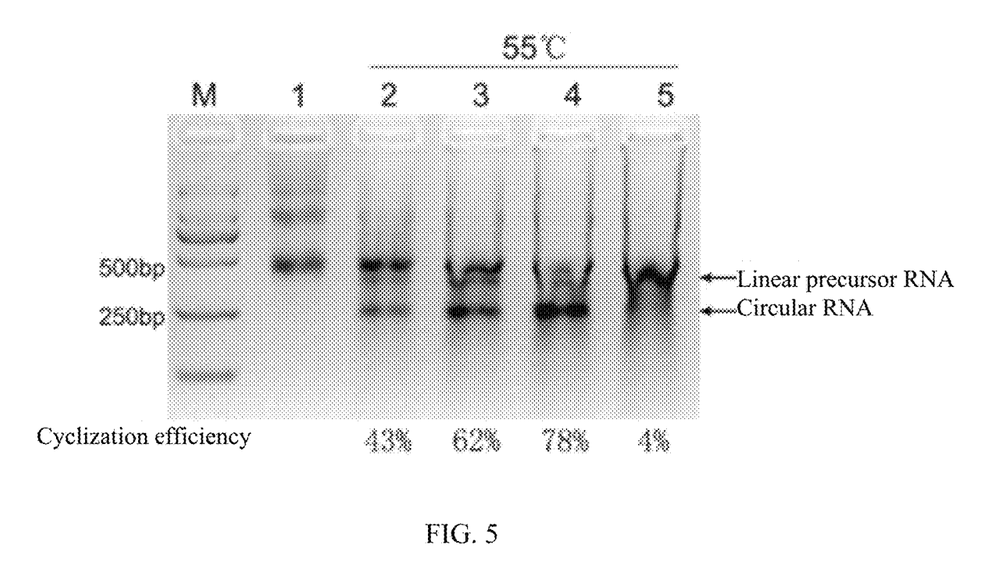
FIG. 5 is a diagram of nucleic acid electrophoresis detection of a circular RNA prepared with an *Anabaena* intron self-cleaving ribozyme at 55° C.

The artificially designed target molecule was subjected to an in vitro cyclization reaction with the above reaction system and conditions through the *Anabaena* intron self-cleaving ribozyme, 0.5 μL of the reaction product was taken, and the cyclization effect was detected through 2% agarose gel electrophoresis. FIGS. 3-5 show the cyclization efficiency at 37° C., 42° C., and 55° C., respectively. In FIG. 3, M: DNA Marker 2000; 1: linear precursor RNA control (no reaction, that is, the purified transcribed linear RNA obtained in the step S4); 2: intron self-cleaving ribozyme reaction product with the linear precursor RNA at a concentration of 1 μg/μL and with a cyclization rate of 18%; 3: intron self-cleaving ribozyme reaction product with the linear precursor RNA at a concentration of 2 μg/μL and with a cyclization rate of 19%; 4: intron self-cleaving ribozyme reaction product with the linear precursor RNA at a concentration of 4 μg/μL and with a cyclization rate of 47%; and 5: intron self-cleaving ribozyme reaction product with the linear precursor RNA at a concentration of 8 μg/μL and with a cyclization rate of 57%.

In FIG. 4, M: DNA Marker 2000; 1: linear precursor RNA control (no reaction); 2: intron self-cleaving ribozyme reaction product with the linear precursor RNA at a concentration of 1 μg/μL and with a cyclization rate of 32%; 3: intron self-cleaving ribozyme reaction product with the linear precursor RNA at a concentration of 2 μg/μL and with a cyclization rate of 37%; 4: intron self-cleaving ribozyme reaction product with the linear precursor RNA at a concentration of 4 μg/μL and with a cyclization rate of 59%; and 5: intron self-cleaving ribozyme reaction product with the linear precursor RNA at a concentration of 8 μg/μL and with a cyclization rate of 75%.

In FIG. 5, M: DNA Marker 2000; 1: linear precursor RNA control (no reaction); 2: intron self-cleaving ribozyme reaction product with the linear precursor RNA at a concentration of 1 μg/μL and with a cyclization rate of 43%; 3: intron self-cleaving ribozyme reaction product with the linear precursor RNA at a concentration of 2 μg/μL and with a cyclization rate of 62%; 4: intron self-cleaving ribozyme reaction product with the linear precursor RNA at a concentration of 4 μg/μL and with a cyclization rate is 78%; and 5: intron self-cleaving ribozyme reaction product with the linear precursor RNA at a concentration of 8 μg/μL and with a cyclization rate of 4%.

Purification of circular RNA: the cyclized product was subjected to gel cutting and purification through agarose gel cutting for recovery with an agarose gel RNA recovery kit (ZYMO) according to the specification of the kit.

Test Example 1 Tolerance Testing of RNase R

The configuration of the RNase R digestion reaction system is shown in Table 4:

TABLE 4

| Component | Usage amount |
| --- | --- |
| \multicolumn{2}{c}{RNase R Digestion Reaction System} | |
| 10× Buffer | 2 μL |
| RNA | 1 μg |
| RNase R | 1 μL |
| DEPC-H$_2$O | Up to 20 μL |

Figure 6:
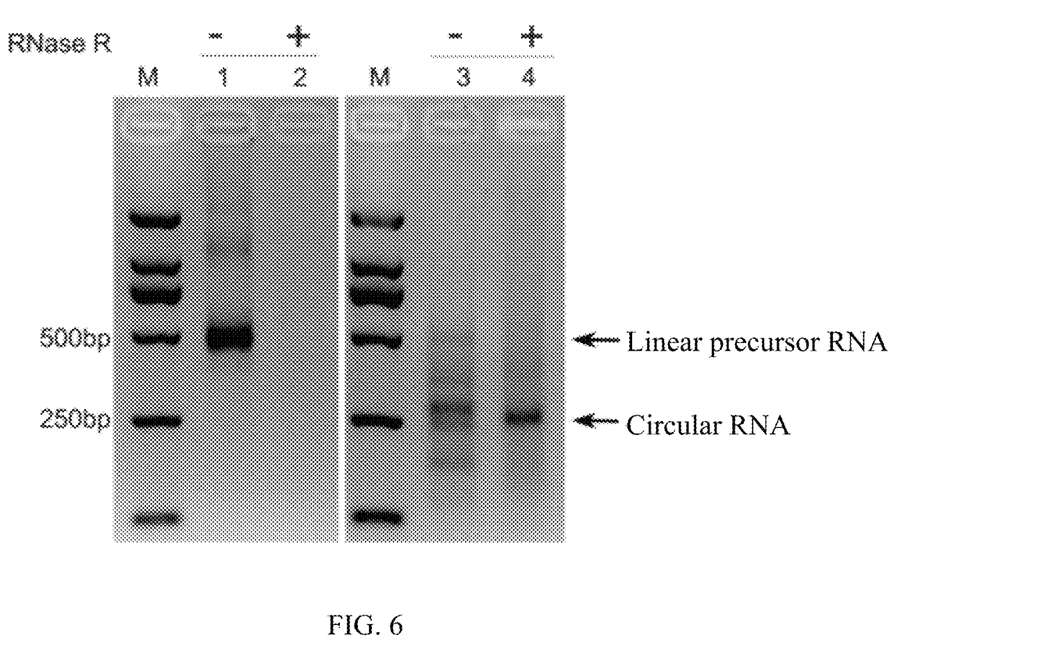
FIG. 6 is a diagram of nucleic acid electrophoresis detection of a circular RNA prepared by RNase R cleavage.

Here, the RNAs were circular RNAs and linear precursor RNAs respectively, which were digested with RNase R enzyme at 37° C. for 15 min and then subjected to 2% agarose gel electrophoresis. The detection result is shown in FIG. 6. In FIG. 6, M: DNA Marker 2000; 1: linear precursor RNA without RNase R; 2: linear precursor RNA with RNase R for digestion for 15 min; 3: circular RNA without RNase R; and 4: circular RNA with RNase R for digestion for 15 min. The RNase R digestion test result shows that the prepared circular RNA is more tolerant of RNase R digestion than the linear precursor RNA.

Test Example 2 Circular RNA Cyclization Interface Verification

Figure 7:
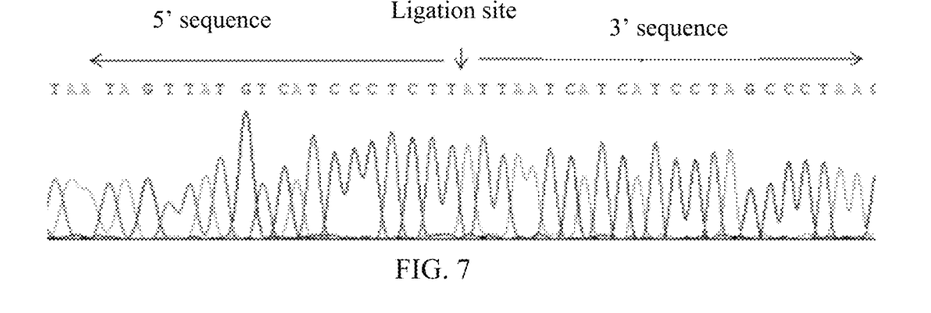
FIG. 7 is a sequencing peak map of an interface sequence (SEQ ID NO.11) of a circular RNA prepared with an *Anabaena* intron self-cleaving ribozyme.

The circular RNA obtained by purification was reversely transcribed into cDNA through a random primer, and PCR primers were designed to detect whether the cyclized product is correct. The PCR primers for identifying whether the cyclized product is correct are as follows: 246 nt-F:5′CTCCTTTTACCCCTACCATG3′ (SEQ ID NO.8) and 246 nt-R:5′GATATAGGGTCGAAGCCG3′ (SEQ ID NO.9). The interface sequence (SEQ ID NO.11) of the cyclized RNA was amplified through PCR. The PCR amplification system is shown in Table 5. The PCR reaction process is as follows: initial denaturation at 95° C. for 5 min first, and then at 95° ° C. for 30 s, at 58° C. for 30 s, and at 72° C. for 30 sin order, 35 cycles in total, and storage at 4° C. Then, the PCR amplification product was sequenced by a sanger method. The sequencing peak map is shown in FIG. 7. The sequencing result shows that the circular RNA can be precisely prepared in vitro with the artificially designed *Anabaena* intron self-cleaving ribozyme.

TABLE 5

| Component | Usage amount |
| --- | --- |
| \multicolumn{2}{c}{PCR Amplification Reaction System} | |
| 2× Taq Master Mix | 25 μL |
| 246nt-F (10 μM) | 2 μL |
| 246nt-R (10 μM) | 2 μL |
| cDNA | 1 μL |
| DEPC-H$_2$O | Up to 50 μL |

Finally, it should be noted that the above embodiments are only intended to exemplarily illustrate the principle, performance, and effect of the present invention but not intended to limit the present invention. Any person of ordinary skill in the art can modify or change the above embodiments without departing from the spirit and scope of the present invention. Therefore, all equivalent modifications or changes made by those of ordinary skill in the art without departing from the spirit and technical ideal disclosed by the present invention should still fall within the claims of the present invention.

What is claimed is:

1. A method for precisely preparing a circular RNA with an *Anabaena variabillis* intron self-cleaving ribozyme, comprising:

S1: analyzing a secondary structure of the *Anabaena variabillis* intron self-cleaving ribozyme, and screening out sequences in upstream and downstream exons that are closely related to the activity of the self-cleaving ribozyme;

S2: selecting an artificial sequence containing the sequences screened out in the step S1, inverting original upstream and downstream intron sequences of the *Anabaena variabillis*, and then replacing an original exon sequence in the *Anabaena variabillis* intron self-cleaving ribozyme with the artificial sequence to form an *Anabaena variabillis* intron self-cleaving frame for preparing the circular RNA;

S3: adding an 18-base reverse complementary sequence to each of the upstream and downstream of the *Anabaena variabillis* intron self-cleaving frame sequence obtained in the step S2, and then adding a T7 transcription promoter to both sides of the sequence and a restriction endonuclease cleavage site to both ends of the sequence to form a total linear RNA sequence, and finally introducing the total linear RNA sequence into a pUC19 skeleton vector to prepare a plasmid;

S4: digesting the plasmid obtained in the step S3 with an endonuclease EcoRI to obtain a linearized plasmid, performing purification, obtaining a transcribed linear RNA through in vitro transcription and DNA template digestion, and performing purification again to obtain a purified transcribed linear RNA; and S5: cyclizing the purified transcribed linear RNA obtained in the step S4 in vitro and performing purification to obtain a purified cyclized RNA, and further performing tolerance testing and circular RNA cyclization interface verification to obtain the circular RNA, wherein the artificial sequence described in the step S2 is shown as SEQ ID NO. 2; the sequence of the prepared *Anabaena variabillis* intron self-cleaving frame is shown as SEQ ID NO. 3; the upstream 18-base sequence described in the step S3 is shown as SEQ ID NO. 4, and the downstream 18-base sequence is shown as SEQ ID NO. 5; the sequence of the T7 transcription promoter is shown as SEQ ID NO. 6; and the total linear RNA sequence is shown as SEQ ID NO. 7.

2. The method according to claim 1, wherein the *Anabaena variabillis* intron self-cleaving ribozyme in the step S1 is shown in SEQ ID NO. 1.

3. The method according to claim 1, wherein the upstream and downstream restriction endonuclease cleavage sites in the step S3 are a BamHI restriction endonuclease cleavage site and an EcoRI restriction endonuclease cleavage site, respectively.

4. The method according to claim 1, wherein the linearized plasmid in the step S4 is obtained as follows: construct a digestion system of 200 μL containing 20 μg of plasmids, 20 μL of 10×Buffer, 10 μL of the endonuclease EcoRI, and DEPC-H$_2$O complementing to 200 μL, and then allow the digestion system to react at 37° C. for 2 h, and finally store the obtained linearized plasmid at 4° C.

5. The method according to claim 1, wherein the in vitro cyclization of the linear RNA in the step S5 is achieved as follows: construct a cyclization system of 400 μL containing GTPs with a final concentration of 0.2 mM, linear RNAs with a final concentration of 2~8 μg/μL, 40 μL of 10×buffer, and DEPC-H$_2$O; mix the cyclization system uniformly and allow it to react at 42° C. or 55° C. for 6 h; finally store the obtained circular RNA at 4° C.

6. A circular RNA obtained by the method according to claim 1.

* * * * *